(12) United States Patent
Mathies et al.

(10) Patent No.: US 6,554,986 B1
(45) Date of Patent: *Apr. 29, 2003

(54) CAPILLARY ARRAY ELECTROPHORESIS SCANNER

(75) Inventors: Richard A. Mathies, Berkeley, CA (US); James R. Scherer, Berkeley, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/579,076

(22) Filed: May 25, 2000

Related U.S. Application Data (63) Continuation-in-part of application No. 09/238,131, filed on Jan. 27, 1999, now Pat. No. 6,270,644.

(51) Int. Cl.$^7$ .................. G01N 27/26; G01N 21/00; G01N 30/02

(52) U.S. Cl. .................. 204/452; 204/603; 356/344; 422/70

(58) Field of Search .................. 356/344; 204/451, 204/452, 601, 603; 422/70

(56) References Cited

U.S. PATENT DOCUMENTS

| | | | |
|---|---|---|---|
| 5,091,652 A | 2/1992 | Mathies et al. | 250/458.1 |
| 5,274,240 A | 12/1993 | Mathies et al. | 250/458.1 |
| 5,354,538 A | 10/1994 | Bunce et al. | 422/100 |
| 5,372,695 A | 12/1994 | Demorest | 204/603 |
| 5,443,791 A | 8/1995 | Cathcart et al. | 422/65 |
| 5,483,075 A | 1/1996 | Smith et al. | 250/458.1 |
| 5,540,888 A | 7/1996 | Bunce et al. | 422/100 |
| 5,560,811 A | 10/1996 | Briggs et al. | 204/451 |
| 5,770,157 A | 6/1998 | Cargill et al. | 422/99 |
| 6,270,644 B1 * | 8/2001 | Mathies et al. | 204/600 |

OTHER PUBLICATIONS

Smith et al., 1986, 321 *Nature* 674–679 Jun.
Swerdlow, H. & Gesteland, R., 1990, 18 *Nuc. Acids Research* 1415–1419.
Luckey et al., 1990, 18 *Nuc. Acids Res.* 4417–4421.
Cohen, A.S. et al., 1990, 516 *Journal of Chromatography* 49–60.
Mathies, R.A. & Huang, X.C., 1992, 359 *Nature*, 167–169, Sep.
E.C. Buxton et al., "Automation in large–scale DNA sequencing," *Laboratory Robotics and Automation* 8 (Abstract) (1996).
Woolley, A. and Mathies, R., "Ultra–high–speed DNA fragment separations using microfabricated capillary array electrophoresis chips," 91 *Proc. Natl. Acad. Sci USA*, 11348–11352, Nov. 1994.
Watson et al., "The Caenorhabditis elegans genome sequencing project: first steps in automation," 362 *Nature*, 569–570, Apr.
Hawkinds et al., "A Magnetic Attraction to High–Throughput Genomics," 276 *Science*, 1887–1889 Jun.
Panussis et al., "A Pneumatic Device for Rapid Loading of DNA Sequencing Gels," *Genome Research* (1998), 543–548.

(List continued on next page.)

*Primary Examiner*—Jill Warden
*Assistant Examiner*—Alex Noguerola
(74) *Attorney, Agent, or Firm*—Pillsbury Winthrop LLP (57) ABSTRACT

An improved rotary confocal fluorescence scanner capable of detecting analytes separated on over a 1,000 capillaries simultaneously. This system uses a confocal microscope objective and mirror assembly that rotates inside a vertical ring of capillaries to provide rapid and efficient excitation and detection of fluorescently labeled fragments separated within a cylindrical capillary array. Use of automated procedures to load and run all capillaries permits one to read more than 350,000 base pairs of raw sequence data per hour.

30 Claims, 10 Drawing Sheets

OTHER PUBLICATIONS

Harrison, D., "Proceedings of the uTAS '98 Workshop, held in Banff, Canada, Oct. 13–16, 1998, "*Micro Total Analysis Systems '98*, 1–7.

Seile, et al., "Planar Glass Chips for Capillary Electrophoresis: Repetitive Sample Injection, Quantitation, and Separation Efficiency," *Anal. Chem.* 1993, 65, 1481–1488 May.

Woolley, A. and Mathies, R., "Ultra–high–speed DNA Sequencing Using Capillary Electrophoresis Chips," *Analytical Chemistry*, vol. 67, No. 20, Oct. 15, 1995, pp. 3676–3680 Oct.

Kheterpal et al., "DNA sequencing using a four–color confocal fluorescence capillary array scanner," *Electrophoresis* 1996, 17, 1852–1859.

D. Schmalzing et al., "DNA Sequencing on Microfabricated Electrophoretic Devices," *Anal. Chem.* 1998, 70, 2303–2310 Jun.

D. Schmalzing et al., "DNA typing in thirty seconds with a microfabricated device," *Proc. Natl. Acad. Sci. USA*, vol. 94, Sep. 1997, pp. 10273–10278.

Simpson et al., "High–throughput genetic analysis using microfabricated 96–sample capillary array electrophoresis microplates," *Proc. Natl. Acad. Sci. USA*, vol. 95, Mar. 1998, pp. 2256–2261.

Woolley et al., "High–speed DNA Genotyping Using Microfabricated Capillary Array Electrophoresis Chips," *Analytical Chemistry*, vol. 69, No. 11, pp. 2181–2186 Jun.

Kheterpal et al., "DNA sequencing using a four–color confocal fluorescence capillary array scanner," *Electrophoresis* 1996, 17, 1852–1859.

Scherer et al., "Ultra–high throughput rotary capillary array electrophoresis scanner for fluorescent DNA sequencing and analysis," *Electrophoresis* 1999, 20, 1508–1517 Jun.

Bevan, C. and Mutton, I., "Use of Freeze–Thaw Flow Management for Controlling and Switching Fluid Flow in Capillary Tubes," 67 *Anal. Chem.*, 1470–1473 (1995) Apr.

* cited by examiner

DNA
SEQUENCING
USING ROTARY
CAE

CAPILLARY ARRAY ELECTROPHORESIS SCANNER

This is a Continuation-In-Part of application Ser. No. 09/238,131, filed on Jan. 27, 1999, which is now U.S. Pat. No. 6,270,644 B1, the disclosure of which is incorporated herein by reference.

NOTICE OF GOVERNMENT RIGHTS

The present invention was made partly with U.S. Government support under a grant from the Advanced Technology Program of the National Institute of Standards and Technology. The government may have certain rights to this invention.

FIELD OF THE INVENTION

The present invention relates to methods and apparatus for separating analytes by capillary electrophoresis. In particular, the present invention relates to capillary array electrophoresis and a method of performing high-speed, high-resolution separations of DNA.

BACKGROUND OF THE INVENTION

The Human Genome Project is driving the development of instrumentation, reagents and methods to achieve the challenging goal of sequencing 3 billion base pairs of human DNA. One new and effective separation technique for nucleic acid analysis is capillary electrophoresis. The use of this technique for DNA sequencing was first demonstrated in 1990 with the separation of approximately 350 bases on cross-linked gels in just over an hour. Since then, a number of groups have improved this technique. Early improvements, for example, utilized in situ polymerized linear polyacrylamide gels and were successful in obtaining high resolution separations. Polymerization reproducibility was problematic with such methods, however, which has driven the development of replaceable gel matrices. One can now read sequences of approximately 1000 bases in 60–90 minutes using capillaries filled with replaceable linear polyacrylamide solutions.

Adapting capillary electrophoresis to high throughput applications requires that one perform separations on arrays of capillaries. The technique, called capillary array electrophoresis, may be performed in conjunction with confocal fluorescence scanning detection, as described in U.S. Pat. No. 5,091,652, the entirety of which is incorporated herein by reference. An improved, four-color version of such detection is described in U.S. Pat. No. 5,274,240, the entirety of which is also incorporated herein by reference.

In the development of capillary array electrophoresis systems, the goal has typically been to run and detect 96 capillaries in parallel. One such system has been commercially developed; it provides automated sample and gel loading of 96 capillaries and is used by high throughput genome centers and pharmaceutical companies. While such systems have proven valuable, it is still desirable to increase their processing power. While these systems may be able to read over 1000 bases per hour, this figure is not so impressive when one considers that the human genome comprises over 3 billion bases.

SUMMARY OF THE INVENTION

It is an object of the present invention to provide an apparatus capable of performing capillary array electrophoresis within more than 96 capillaries, and to detect the analytes thus separated. It is a further object of the invention to perform such separation at high speed, suitable for the most demanding high-throughput applications. It is a particular object of the invention to enable detection of over 1,000 bases per hour, and to provide a system compatible with known automation techniques. Yet another object of the invention is to provide for an improved detection apparatus, capable of detecting in four colors the analytes separated.

Described herein is an improved rotary confocal fluorescence scanner capable of detecting analytes separated on over 1,000 capillaries simultaneously. This system uses a confocal microscope objective and mirror assembly that rotates inside a vertical ring of capillaries to provide rapid and efficient excitation and detection of fluorescently labeled fragments separated within a cylindrical capillary array. Use of automated procedures to load and run all capillaries permits one to read more than 350,000 base pairs of raw sequence data per hour.

DETAILED DESCRIPTION OF THE INVENTION

Figure 1:
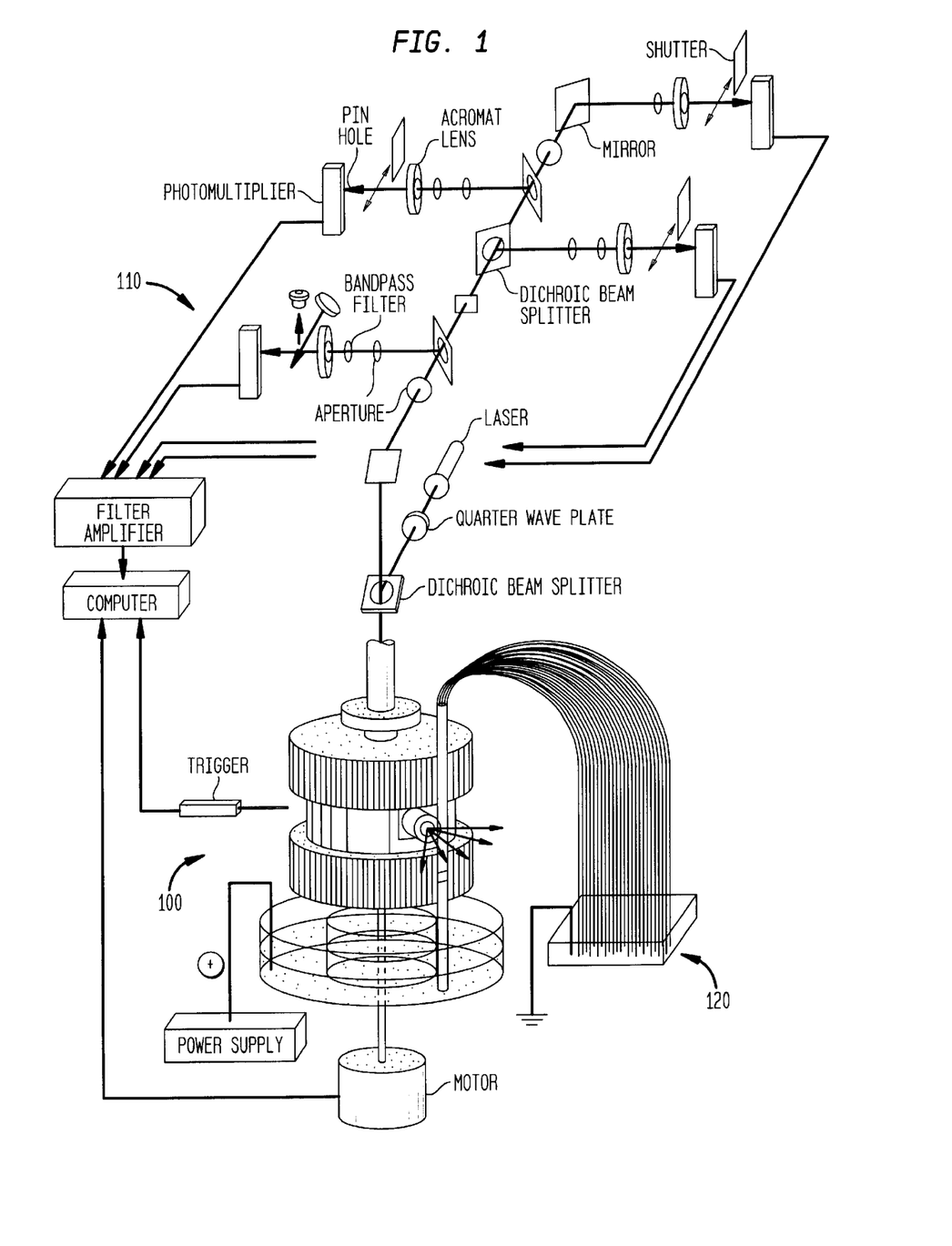
FIG. 1 is a schematic diagram of a high-capacity rotary scanner and a four-color confocal fluorescence detection system.

FIG. 1 is a schematic overview of a preferred embodiment of the invention employing a four-color confocal detection system. A 488 nm argon ion laser excitation beam is deflected downward into the scanner head with a dichroic beam splitter. A 45° diagonal mirror located in the central rotor of the scanner head directs the beam horizontally to an objective that focuses the beam onto capillaries. The capillaries are mounted in grooves along the sides of two cyclinders, each of which is approximately four inches in diameter. The cylinders are capable of accommodating over 1,000 capillaries. For ease of mounting, the capillaries are grouped into bundles, each containing 32 capillaries. Fluorescence from the capillaries is collected by the objective and passed to the four-color confocal detection system. This arrangement permits easy detection of fluorescence from over 1000 capillaries with a single compact scanner.

Figure 2:
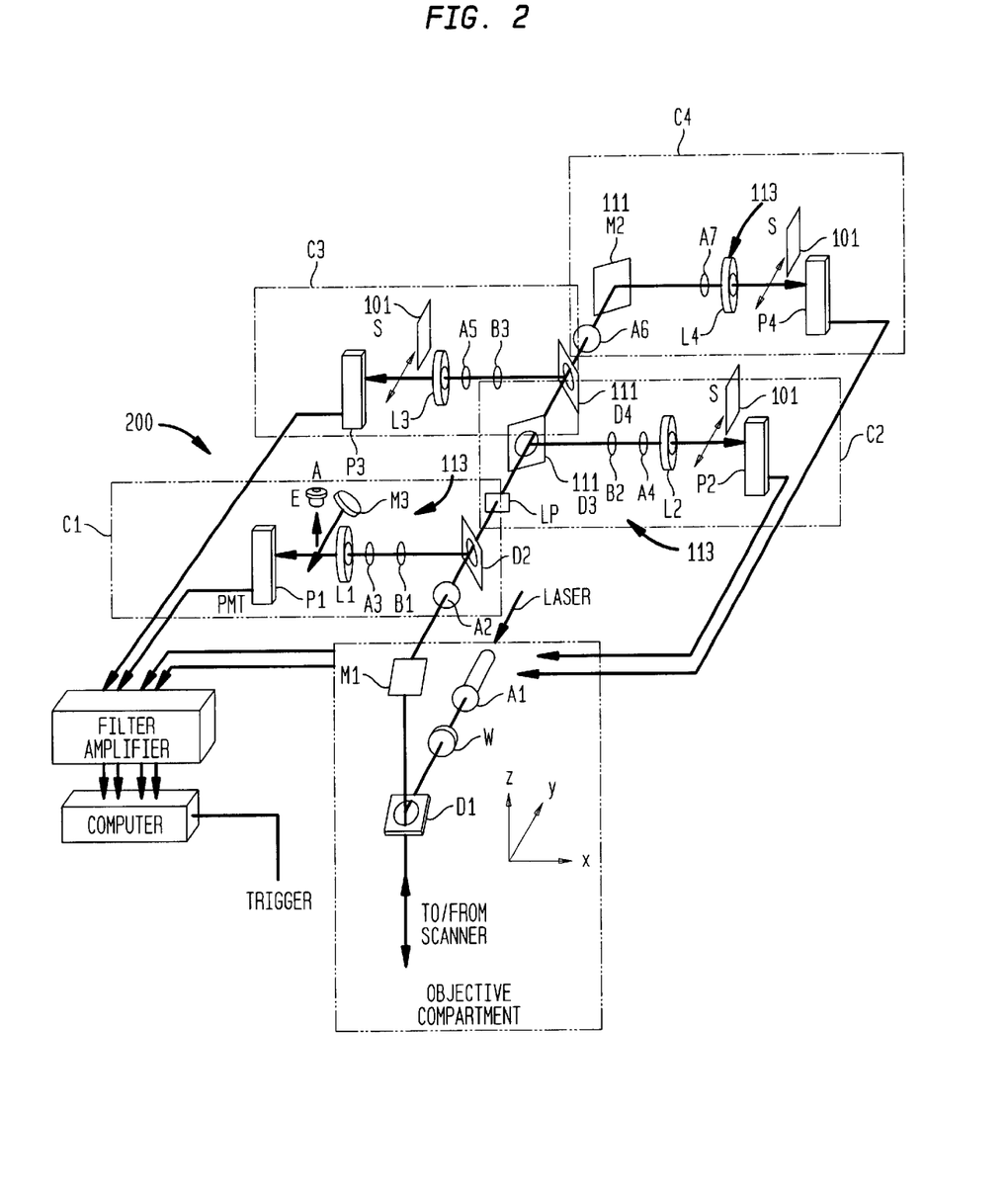
FIG. 2 is a schematic diagram of a four-color confocal fluorescence detection system.

FIG. 2 is a schematic diagram of a presently preferred embodiment of a detection system which may be used with the present invention. The system is a four-color confocal detection system described in detail in I. Kheterpal et al., "DNA sequencing using a four-color confocal fluorescence capillary array scanner," *Electrophoresis* 1996, 17, 1852–1859, incorporated herein by reference, and described again here.

For convenience of description, the four-color detection system comprises five connected compartments: one for sample excitation and fluorescence (called the objective compartment OC), and four sequential modular color-detection compartments C1, C2, C3, and C4.

The scanning beam in this system is a beam of coherent radiant energy, such as that produced by a laser. An argon ion laser is preferred, though one may use other lasers, such as a tunable dye laser or a diode laser, or one may not use a laser at all: any monochromatic light source having appropriate wavelength range and light intensity may be employed in the practice of the invention. The label "LASER" of FIGS. 1 and 2 is therefore used for convenience only, as one may employ non-laser sources of radiant energy in the practice of the invention. Preferred sources of radiant energy lasers include a Model 2017 argon ion laser made by Spectra-Physics of Mountain View, Calif., and ion lasers available from Coherent Radiation of Santa Clara, Calif. An especially preferred source of radiant energy is a Spectra Physics Model 2020 argon ion laser.

The source of radiant energy is placed anywhere it will not interfere with the operation of the other components of the invention. In the embodiment illustrated in FIG. 2, for example, the source of radiant energy is placed under the color detection units P1, P2, P3, and P4.

The appropriate wavelength and intensity of radiant energy will depend on the analytes to be separated and the resolution of detection desired. For DNA, RNA and other fluorescing labeled analytes, a wavelength of radiant energy between approximately 450 nm to 550 nm and an intensity of between approximately 1 mW to 500 mW would be appropriate. For DNA sequencing fragments, a preferred wavelength of radiant energy is 488 nm and a preferred intensity is approximately 350 mW for scanning velocities of 130 cm/s.

In the preferred embodiment illustrated in FIG. 2, a laser beam having a wavelength of 488 nm and intensity of approximately 250 mW emerges from the laser to define a y-axis of propagation (the z and x axes are perpendicular to the y-axis in the conventional manner). The beam is expanded by 10 times upon emerging from the laser, and is then passed through a collimating lens (not shown). From the collimating lens, the beam is directed to an iris diaphragm A1, which limits the aperture of the beam to approximately 5 to 15 mm. In a preferred embodiment, the aperture is reduced to approximately 9 mm. In order to make the intensity and polarization of the laser beam at the capillaries independent of rotor position, a quarter wave plate (488 nm) W is inserted between the laser and the dichroic beam splitter D1.

Dichroic beam splitter D1 is positioned at an angle so as to deflect the beam to an objective lens (FIG. 3, 120) within the scanner. In a preferred embodiment, dichroic beam splitters D1, D2, D3, and D4 are all positioned at an angle of 45° in the manner shown in FIG. 2. At this angle, dichroic beam splitter D1 deflects the beam downward along the z-axis (−z). The proper position of dichroic beam splitters D1, D2, D3, D4 will depend on the transmission efficiency and spectral purity characteristics of the dichroic beam splitters used, the wavelength of radiant energy which passes through them, and other factors apparent to one of ordinary skill in the art. The configuration shown in FIG. 2 is thus a preferred configuration, but only one of several other possible configurations. D1, however, should be positioned at 45° to the incident beam in order to make the reflection and transmission characteristics suitable for dye excitation and fluorescence transmission. In addition, the beam reflected from D1 must coincide with the rotation axis of the scanner.

In the embodiment illustrated in FIG. 2, dichroic beam splitter D1 reflects wavelengths of 425–490 nm. The upper limit of this range is higher than the wavelength of the laser beam in this embodiment; accordingly, dichroic beam splitter D1 reflects the laser beam down (−z) into the scanners.

Dichroic beam splitters D1, D2, D3, and D4 preferably have the characteristics summarized in Table 1. In a preferred embodiment, these beamsplitters are models 505DRLP, 535DRP, 570DRLP, and 595DRLP, available from Omega Optical, Inc. of Brattleboro, Vt. Each dichroic beam splitters is used in conjunction with a bandpass filter. Presently preferred such filters, also available from Omega Optical, are also listed in Table 1.

TABLE 1

Preferred Dichroic Beam Splitter Characteristics at 45° incidence

| BEAM SPLITTER | REFLECTION AT 488 NM | REFLECTION REGION (RANGE NM > 90% R) | TRANSMISSION REGION (NM > 50% T) | BANDPASS FILTER |
| --- | --- | --- | --- | --- |
| 1 | 98% | 425–490 | 505 | none |
| 2 | 74% | 497–548 | 560 | 520DF30 or 525DF30 |
| 3 | 20% | 520–567 | 578 | 552DF30 or 555DF30 |
| 4 | ~26% | 495–585 | 596 | 580DF26, or 580DF24 |

Figure 3:
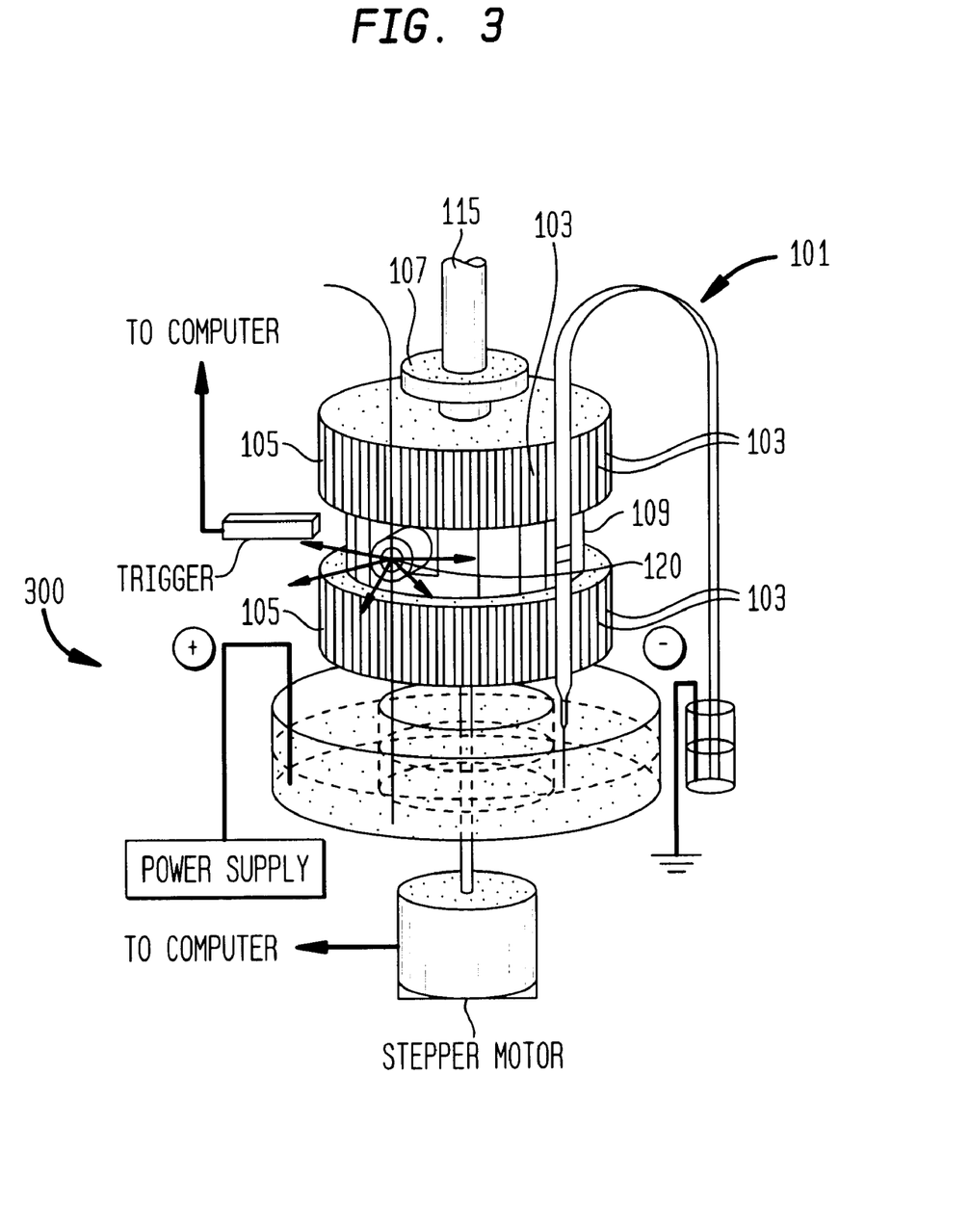
FIG. 3 is a schematic diagram of a high-capacity rotary scanner.

Referring to FIG. 3, a mirror (not shown) positioned within the scanner at an angle of 45° directs the laser beam outward in the xy plane to an objective lens 120. In a preferred embodiment, the objective lens 120 is an achromat microscope objective having a focal length of 9 mm and a numerical aperture (N.A.) of 0.5. A preferred such lens is manufactured by Rolyn Optics of Covina, Calif. The objective lens may also be an achromat lens, and may be either flat field or plano lens. All such lenses are preferably used with an infinite conjugate.

Capillaries 101 are placed against grooved disks 103, ensuring that the capillaries all lie in the same focal plane and with the same periodicity. The capillary surface has a high curvature at the glass/air interface. Consequently, rays entering the objective lens within the xy plane are focused to a line within the capillary nearest the objective (axial focus) and rays entering along the z direction are focused to a line furthest from the objective (transverse focus). The difference between the focii can be as much as 50–75 $\mu$m depending on the inside and outside diameter of the capillary and the numerical aperture (NA) of the objective. One can achieve smaller excitation volumes by decreasing the NA (this is contrary to the usual correlation between NA and diffraction-limited spot size when focusing through plane surfaces).

Referring again to FIG. 2, fluorescence from the capillaries is collected by the objective (at full NA), passed through dichroic beam splitter D1, and deflected by mirror M1 (through iris diaphragms A2 and A6) into the first of the four-color detection compartments C1. Dichroic beamsplitter D2 reflects wavelengths 497–548 nm and the bandpass filter B1 limits the wavelength range to 510–540 nm. Iris diaphragm A3 and the location of pinhole P1 are used to define the unfocused beam path and the 45° dichroic position. A presently preferred pinhole is available from Melles-Griot of Boulder, Colo.

An achromat lens L1, having a focal length of 105 mm and xyz adjustment, focuses the color-filtered beam on a 200 $\mu$m confocal pinhole P1. A preferred such lens is available from Rolyn Optics. A diagonal mirror M3 is mounted so as to be movable in and out of the beam path between L1 and P1. Mirror M3 creates an image plane at the top cover of the compartment C1, and a 20× Ramsden eyepiece E is used to view the image plane. A preferred 20× Ramsden eyepiece is available from Rolyn Optics. Light passing through the pinhole P1 is detected by a photomultiplier tube PMT1. Preferred models of photomultiplier tube are the Hammamatsu HC120-05 and HC120-07, available from Photonics Research Corp. of San Jose, Calif., though other photomultiplier tubes having similar response may be used, as well.

The beam that passes through dichroic beam splitter D2 enters the second compartment C2, the components of which are substantially similar to those in the first detection compartment C1. A removable longpass glass filter LP is used for additional blocking of the laser wavelength. A preferred longpass glass filter is the OG530, available from Omega Optical. OG530 is a universal glass designation, and is independent of the manufacturer of optical equipment used.

Each successive compartment measures a longer wavelength range defined by the respective bandpass filters. Compartments 2, 3 and 4 (C2, C3, and C4) have a sliding shutter S in place of a diagonal mirror to block light from entering the photomultipliers PMT2, PMT3, and PMT4. Compartment 4 (C4) contains a mirror in place of a dichroic beamsplitter and no bandpass filter is used to limit the long wavelength detection range. Plasma lines in the primary laser beam are significant beyond 590 nm and are removed using a line filter. A preferred line filter is the Newport 1OLF10-488, available from Newport of Irvine, Calif.

The outputs of the photomultiplier tubes PMT1, PMT2, PMT3, and PMT4 are amplified and filtered using analog low-pass filters, the signal from which is digitized using a 12 to 16 bit analog-to-digital converter. The converter should operate at frequencies consistent with the sampling rate and selected number of data points/revolutions. A preferred such converter is the 3400a, available from Microstar Laboratories of Bellevue, Wash. The analog filter should be appropriate for the data acquisition rate of the converter. A preferred such filter is the SR 640, available from Stanford Research Systems, Inc. of Sunnyvale, Calif. The intensity data are collected uni-rotationally and stored in a computer for processing.

Aligning the Laser Beam

The primary laser beam is adjusted parallel to the y direction and intersect the center of the iris A1 at the entrance to the objective compartment OC. A far aperture (not shown) is placed in the laser beam path about one to three feet, and preferably two feet before entering iris A1. A parallel front surface mirror is placed on a horizontal platform on top of the scanner head that is perpendicular to the rotation axis. D1 is adjusted so that the laser beam returns on itself; to make this adjustment, all dichroic beam splitter of the invention (as well as all mirrors) are preferably equipped with mechanisms that allow orthogonal adjustments. The unaligned return beam can be seen on the instrument side of the far aperture. Mirror M1 is adjusted to make the beam transmitted by D1 pass through $A_2$ and $A_6$. Lens L1 and band-pass filter B1 are removed and dichroic beam splitter D1 is positioned to make the beam pass through the middle of lens A3 and center on pinhole P1. Photmultiplier tube P1, fastened on the outside of the compartments, is removed and lens L1 is replaced. A white card is placed a small distance beyond the pinhole P1 and lens L1 is adjusted (yz) to pass the focused beam through the pinhole P1. The pinhole diameter is approximately 100 $\mu$m to 300 $\mu$m, and preferably 200 $\mu$m, and is much larger than the spot size produced by lens L1 and can be used, as in the standard "knife edge test," to establish the focal distance for lens L1. The focus of lens L1 (position of minimum beam waist) is moved (along x) until small translations of L1 in they or z direction produce sudden complete cut-off or turn-on of the beam. Since the laser beam in front of lens L1 is parallel, the objective will be forced to function as if it had an infinite conjugate (even though it has no corrected infinite conjugate), thereby ensuring that the subsequent compartments will be sampling the same confocal region within the capillaries. The beam is left centered on the pinhole P1. The optics in the remaining compartments C2–C4 are adjusted in a similar manner and the photomultiplier tubes PMT2, PMT3, and PMT4 are refastened on the exterior housings. Bandpass filters B1–B3 and longpass filter LP are replaced. The mirror on the horizontal platform is removed and the plane glass optic is tilted to center the beam on the objective aperture.

The capillaries are placed in grooves around the cylinders (FIG. 3, 103) and the laser beam brought to a focus within the flowing solution. Final adjustments on the optics are made by translating the objective within its mount (in the xy plane) until maximum fluorescence intensity is achieved. Once this is accomplished, the focus of the objective is fixed and need never be checked because of the invariance of the focal distance with rotation. The focal region may be observed visually by moving the diagonal mirror M3 to intercept the beam between lens L1 and pinhole P1, and adjusting the eyepiece to bring the bright fluorescence cross, caused by the two capillary focii, into sharp focus. Fine tuning of the intensity is done by taking M3 out of the beam path, removing the covers of the compartments in a darkened room and applying voltage to the photomultipliers. The signal from compartment 1 (C1) is maximized by making the image of the sample volume fall in the center of the pin hole through lateral adjustments (yz) on lens L1. Once the overall alignment has been established, one skilled in the art and familiar with the system can reoptimize it daily in under 20 min.

In a preferred embodiment, the solution used to perform the final adjustments is a 1 nM fluorescein solution in a 1×TBE buffer (i.e., a buffer comprising 90 mM Tris, 90 mM boric acid, and 2 mM EDTA) having a pH of 8.0. Other solutions may be used as well, as long as they contain materials that can be excited with the source of radiant energy used and fluoresce in the region of 500 to 600 nm.

The capillaries used to adjust the focal region must have the same ID and OD as the capillaries that are to be used in sequencing measurements. In a preferred embodiment, the capillary has an ID of 100 $\mu$m and an OD of 200 $\mu$m.

In alternative embodiments, the detection system may comprise a single dichroic beam splitter and a single photomultiplier tube. Such a system is described in U.S. Pat. No. 5,091,652. Alternate embodiments of a detection system employing four dichroic beam splitters and four photomultiplier tubes is described in U.S. Pat. No. 5,274,240. Additional colors can be added in an obvious fashion, designed to detect additional analytes.

FIG. 3 illustrates the scanner head, comprising a pair of grooved cylinders 103 on which a capillary bundle 101 has been mounted. An objective lens 120 is mounted on a rotor (not shown) which is driven by stepper motor. The motor may be a micro-stepping indexed motor. The rotor 120 rotates the lens at speeds of 1 to 10 revolutions per second, and preferably at speeds of 2 to 4 revolutions per second. The rotor is supported by two precision bearings that are attached to the grooved cylinders 101. The cylinders are rigidly attached to four support posts, shown in FIG. 4, which are accurately spaced by four pairs of aluminum rings defining the positions of the four quadrants. Each of the aluminum rings support eight U-shaped plastic fixtures that press the capillaries firmly against the grooved cylinders. These fixtures are driven inward by 0–80 screws centered on the aluminum rings. The support posts (C) are pinned and bolted to mounts anchored onto the optical table, thereby allowing removal and replacement of the whole head assembly without disrupting the optical alignment of the scanner. The rotor shaft below the lower bearing is attached to a stepper motor (M) through a flexible coupling. The sides of the cylinders (B) are divided into 1200 positions in four quadrants. Each quadrant contains from approximately 10 to 50 positions assigned to support post areas without capillaries and from approximately 100 to 300 grooves for capillaries. In a preferred embodiment, each quadrant contains 28 positions without capillaries and 272 grooves for capillaries. The grooves are spaced by approximately 200 $\mu$m to 300 $\mu$m and are from 75 $\mu$m to 175 $\mu$m deep. In a preferred embodiment, the grooved are spaced by 260 $\mu$m and are 127 $\mu$m deep. Capillaries are bundled to make mounting easier, depending on the number of capillaries used. In a preferred embodiment, for examples, eight bundles of 32 capillaries occupy one quadrant, with two unoccupied grooves left between each bundle. The spaces between bundles are left to ensure that the U-shaped fixtures that clamp a group of capillaries positively hold the first and last capillary in that group. This attachment system insures that all capillaries are at the focus of the objective as it swings around the cylinder.

The capillary bundles are connected to a high pressure reservoir by means of a 1" thick lucite adaptor plate (H), which is attached through four posts to the bottom of the lower grooved cylinder (B). A mating Lucite cylinder (L) contains a trough (K), isolated by two O-rings, that holds matrix material that is forced into the capillaries under pressure. The ends of the capillary bundles extend about ½" beyond the bottom of the adaptor plate and reach near the bottom of the trough (L) when it is bolted to the adaptor plate (H). The assembly (L) is secured to the adaptor plate by means of eight ¼-20 bolts around the central area and sixteen bolts (the clearance holes are visible in this quadrant) around the perimeter of (L). A ring containing threaded holes for the central bolts and four separate quarter rings for the outer bolts facilitate the assembly process.

Fabrication and Mounting of Capillary Arrays

Figure 4:
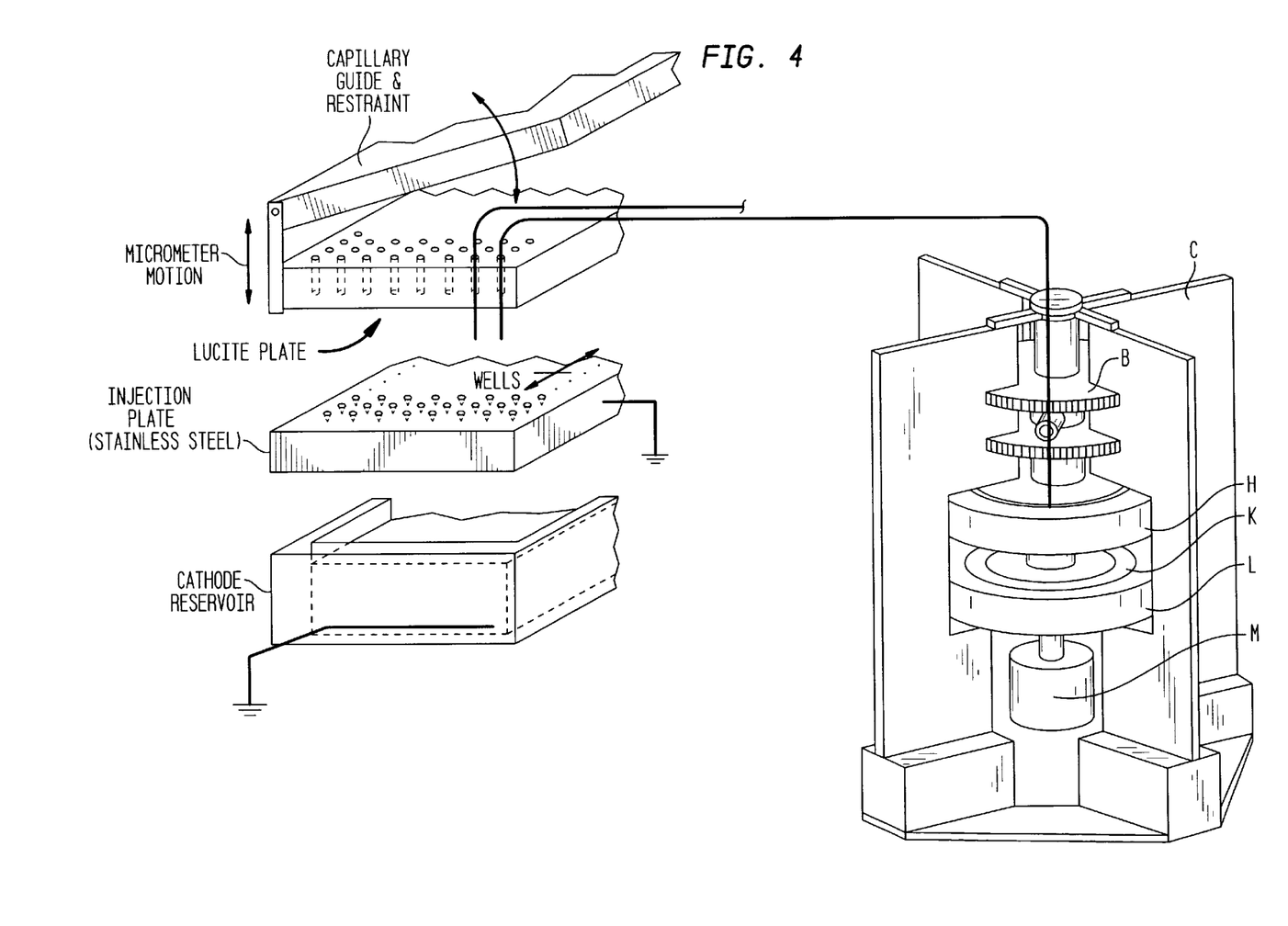
FIG. 4 is a schematic diagram of a rotary scanner connection to a electrokinetic injection assembly illustrating the capillary guide plate, the stainless steel injection plate, and the running buffer reservoir.
Figure 5:
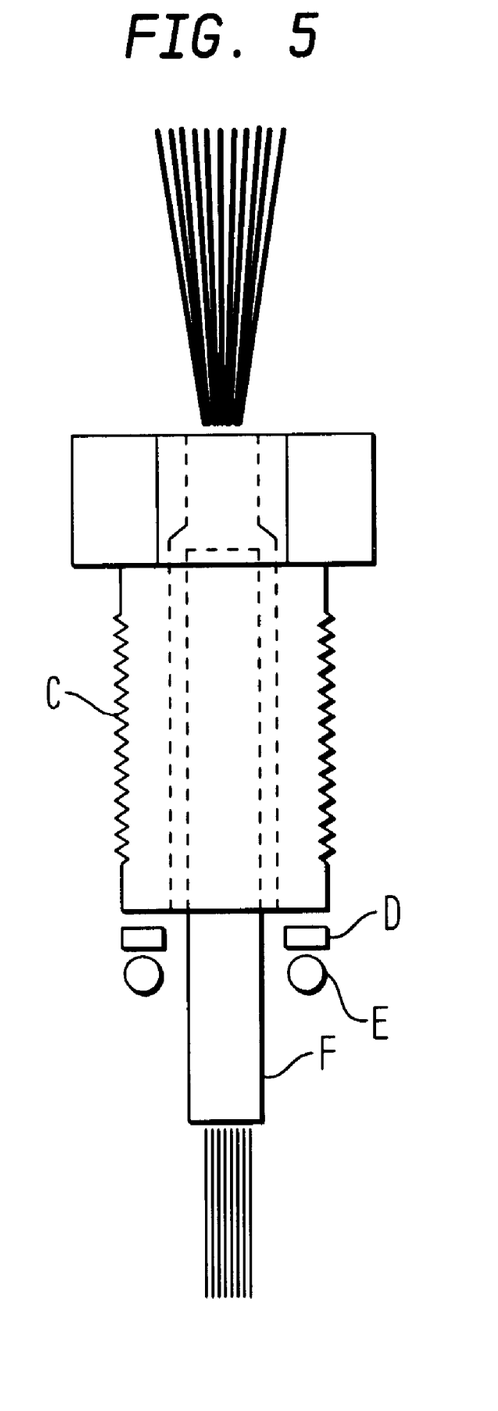
FIG. 5 is a schematic diagram of a bundle of 32 capillaries held together by a bead of epoxy, in which the capillaries are threaded through a modified high-pressure PEEK fitting.

FIG. 5 illustrates a capillary bundle and a high pressure fitting that attaches the bundle to the adaptor plate. The capillaries have an OD of approximately 100 to 300 $\mu$m, although capillaries with an OD of approximately 180 $\mu$m are preferred. These are mounted in a separate grooved fixture with identical spacing as is used in the scanner. The capillaries are cemented together with 5 min epoxy (A) at places just outside the clamping positions of the U-shaped blocks shown in FIG. 4. The capillaries are gathered together at the anode end, and inserted through a modified PEEK HPLC fitting with 10–32 threads (C) and sealed with epoxy cement to the inside of a 15 Ga. stainless steel tube ⅜ inches long (F). The PEEK fitting screws into the adaptor plate without rotating the capillary bundle and a high pressure seal is made when the stainless steel washer (D) compresses the O-ring (E) against a shoulder in the mating cavity in the adaptor plate. The windows (B) are formed by burning the polyimide off with hot sulfuric acid. The capillaries are gathered together, threaded through a modified high-pressure PEEK fitting with 10–32 threads (C), and epoxied into a stainless steel sleeve (F). A washer (D) and O-ring (E) provide the seal to the mating cavities in the adaptor plate (FIG. 4, H).

Data Acquisition

The rotating laser beam initiates data acquisition by means of a light pulse from an optic fiber, preferably with a diameter of approximately 200 $\mu$m, placed in the focal region ahead of the first capillary to be measured. The fiber optic feeds a remote photodiode that produces a pulse that initiates simultaneous data collection from four independent 12-bit ADCs on a data acquisition board. A preferred such board is the 3400a, manufactured by Microstar Laboratories, of Bellevue, Wash.

In an alternative embodiment, one can initiate data acquisition by mounting a thin disk to the shaft of the stepper motor. The disk has a slot disposed at least part way along an axis defining the radius of the disk, preferably forming an opening near the disk's edge. A command diode emitter/receiver is positioned at the edge of the disk. The rotating slot provides a pulse every revolution of the disk, and the timing of the pulse is positioned, by rotating the disk along the shaft, to occur in the gap between one of the quadrants.

Sample times may be from 5 to 15 us per data point, although 11.55 us per data point is preferred. The rotation speed of the rotor is set to match the data rate to give from 10 to 20 data points across the repeat spacing of the capillaries. In a preferred embodiment, the rotation speed is set to 4.008337 rev/e to give exactly 18 data points (86.4 Khz data rate). The precision of the rotation is such that the last capillary to be measured in one rotation is in exact registration with its expected data position.

Figure 7:
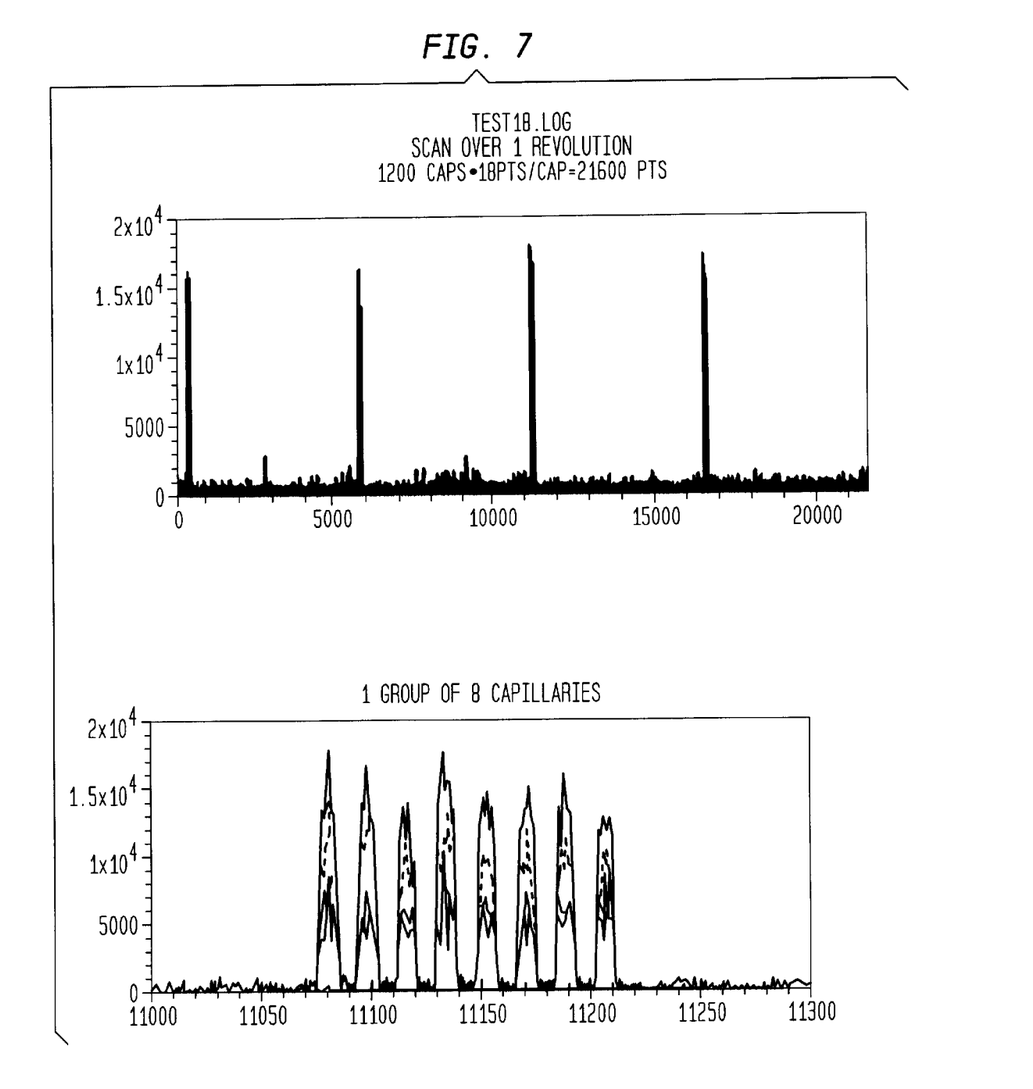
FIG. 7 depicts intensity values for a fluorescence signal from a 1 nM fluorescein solution obtained in one revolution at 4 rps from groups of eight capillaries at the beginning of each of four quadrants of the scanner.

To demonstrate the positional accuracy of the scanner, one can arrange groups of eight capillaries at the beginning of each of the four quadrants of the scanner. A 1 nm fluorescein solution in 1×Tris-borate-EDTA (TBE) is circulated through 32 capillaries; the fluorescence signals detected during one rotation of the scanner (21,600 data points) are shown in FIG. 7 (top). The blue, green, black and red traces are the signals from channels 1–4 (520, 550, 580, >600 nm), respectively. The peak intensities for all four groups are approximately the same, demonstrating the constant focal depth of all capillaries around the cylinder. FIG. 7, (bottom) presents an expanded view of the data from the group of eight capillaries in the third quadrant. The registration of the capillaries is such that the 21,600 data points of a full revolution accurately match the physical locations of the capillaries. The data stream consists of ten 12-bit data points (for each color) from the capillary and eight data points from the intervening space (repeat spacing of 260 $\mu$m). The reproducibility of subsequent scans is determined by the reproducibility of the triggering and motor velocity control. The jitter in the position of the band of intensity from any capillary on subsequent cycles is within one data position. The algorithm used to isolate data from the sample regions of the capillary takes this uncertainty into account by averaging 14 data points centered on each capillary position. The ADC board contains its own 486 microprocessor and performs data stripping and averaging both across the capillaries and for successive cycles in multi-tasking real time. The raw data acquisition rate for the four channels at 4 Hz is 345,600 12-bit samples per second. However, the processed data rate is only 16,384 data points per second (1022 data positions×4 colors×4.008337 Hz). A rotation speed of 4 rev/s was chosen to ensure that all the DNA fragments passing through the 20 $\mu$m long detection zone of the capillary are interrogated.

Signal to Noise Optimization

Rotary scanning enables rapid and smooth beam motion that is essential for high-speed interrogation of a large number of capillaries. The consequence of these conditions for the limiting signal-to-noise ratio can be considered with reference to theories of fluorescence detection optimization, such as those set forth, for example, in R. A. Mathies et al., *Analytical Chemistry*, vol. 66, at 1424–1431 (1994). In the present invention, the detection zone of the preferred 340 mW ($8.5\times10^7$ photons per second) laser beam is approximately a 20×20 $\mu$m area and the transit time of the 20 $\mu$m beam past a pixel is approximately 16 $\mu$s at a scan rate of 4 Hz. For fluorescein this gives a dimensionless excitation intensity ($\kappa$) of approximately 0.3 and a dimensionless transit time ($\tau$) of approximately 0.1 based on a photodestruction quantum yield of $2.7\times10^5$. These parameters are better than those used for linear scanners ($\kappa=-0.006, \tau=-13$) and are close to the optimum for laser-excited fluorescence detection. This results in near-optimal interrogation of all of the analyses illuminated by the beam. Furthermore, the velocity of an ~300 base sequencing fragment is ~100 $\mu$m/s; the 4 Hz data acquisition rate therefore interrogates ~80% of the fragments in a typical electrophoretic band. The width at half-height for a 300 base band is ~4 s, which leads to 16 data points over the half-width. Fragments of smaller size will be somewhat under-sampled while larger fragments will be oversampled. Nevertheless, the effective duty cycle of this high-speed scanning system is within a factor of two of that available in continuous illumination and CCD imaging detection and the photophysical properties are near optimal. The limits of detection of this system were determined by flowing fluorescein at varying concentrations through the capillaries. Scanning at 2 Hz with 600 mW of laser power and a flowing fluorescein solution, one finds that the difference signal (510–530 nm) between 10 PM fluorescein and water can be observed with a signal-to-noise ratio of 2. The optimum laser power is determined by observing fluorescence from a capillary filled with 1 nM fluorescein solution in 1×TBE and increasing the laser power until the signal reaches a plateau. At these power levels (typically ~300 mW) there is no degradation of signal in a stationary fluorescein solution when scanned at 2–4 Hz. This indicates that at these rotation velocities, the illumination time is below the photodestruction time and that the signal is limited by ground state depletion and the number of fluorescent molecules present. Diffusion between scans replaces molecules as fast as they are destroyed.

Capillaries, Sieving Matrix and Samples

Fused-silica capillaries (50 cm long, 75 $\mu$m ID, 180 $\mu$m OD) are preferably precoated with acrylamide. One may obtain such capillaries from Polymicro Technologies of Phoenix, Ariz. One preferably surface-treats these using a Grignard reaction and coated with 3% acrylamide according to the procedure described by Dolnik et al., *Journal of Microbiology*, Vol. 10, pg. 175–184 (September 1998). The capillaries are then cut and bundled into groups of 32 as described above. Windows in the capillaries are burned approximately 8.1 cm from the anodic end using hot concentrated sulfuric acid. Preferably, one then uses a replaceable linear polyacrylamide (LPA) sieving matrix prepared according to the procedure of Carrilho et al., *Analytical Chemistry*, Vol. 68, pg. 3305–3313 (1996), with slight modifications: a 6% solution of acrylamide in 10 mL of water is degassed under helium for half an hour followed by addition of 5 $\mu$L of 10% TEMED (Bio-Rad, Hercules, Calif.) and 10 $\mu$L of 10% APS (ammonium persulfate; Bio-Rad) at 0° C. The polymerization is allowed to proceed for 24 h at 0° C. The polymerized gel was diluted to a final concentration of 3% in 7 M urea and 50 mM Tris, 50 mM N-tris (hydroxymethyl)methyl-3-aminopropanesulfonic acid (TAPS) and 2 mm EDTA buffer. DNA sequencing samples are synthesized using M13mp18 single-stranded templates, cyanine donor energy transfer (ET) primers, such as those described in S. C. Hung, et al., *Analytical Biochemistry*, Vol. 252, pg. 78–88 (1997), and Thermo Sequenase (available from Amersham Life Science, Cleveland, Ohio) following the Sanger dideoxy method, as described in Sanger et al., *Proceedings of the National Academy of Sciences*, Vol. 74, pg. 5463–5467 (1977).

DNA may be sequenced as follows. Four DNA sequencing reactions are set up, one for each dye/ ddNTP pair. C10R110, C10G, C10T and C10R primers were used to label reactions terminated with ddCTP, ddTTP, ddGTP and ddATP, respectively. For each reaction, 1 $\mu$L of the pre-mix from the Thermo Sequenase kit is mixed with 0.4 pmol of the primer and 0.2 $\mu$g of the template DNA. Twenty cycles (95° C. for 45 s, 45° C. for 30 s and 70° C. for 45 s) are performed followed by ethanol precipitation. The precipitated DNA is dissolved in 4 $\mu$L of 70% deionized formamide for loading.

Sieving Matrix Loading

The capillaries are filled with replaceable LPA by loading the matrix into the well (FIG. 4, K) and forcing it into the capillaries with He gas under pressure. The well is filled with replaceable sieving matrix using a syringe. The upper and lower lucite plates are bolted together and the trough is pressurized to fill the capillaries. The unit should be pressure-tested to withstand approximately 1000 psi. Preferably, the capillaries are filled with 3% LPA at ~400 psi in 10 min. After filling the capillaries with matrix, the lower pressure chamber is unbolted and lowered and two half-wells containing running buffer and electrodes are bolted to the upper adaptor plate (FIG. 4, H). The polymer-filled capillaries are pre-electrophoresed for 10 min at 100 V/cm. Separations may be carried out with fields up to 200 V/cm and the total current in this system can exceed 10 mA. To provide adequate safety, one should use two power supplies individually fused at 6 mA and two independent running buffer anode wells. The running buffers in both the anode and cathode reservoirs can be recirculated with peristaltic pumps.

Sample Loading

Figure 6:
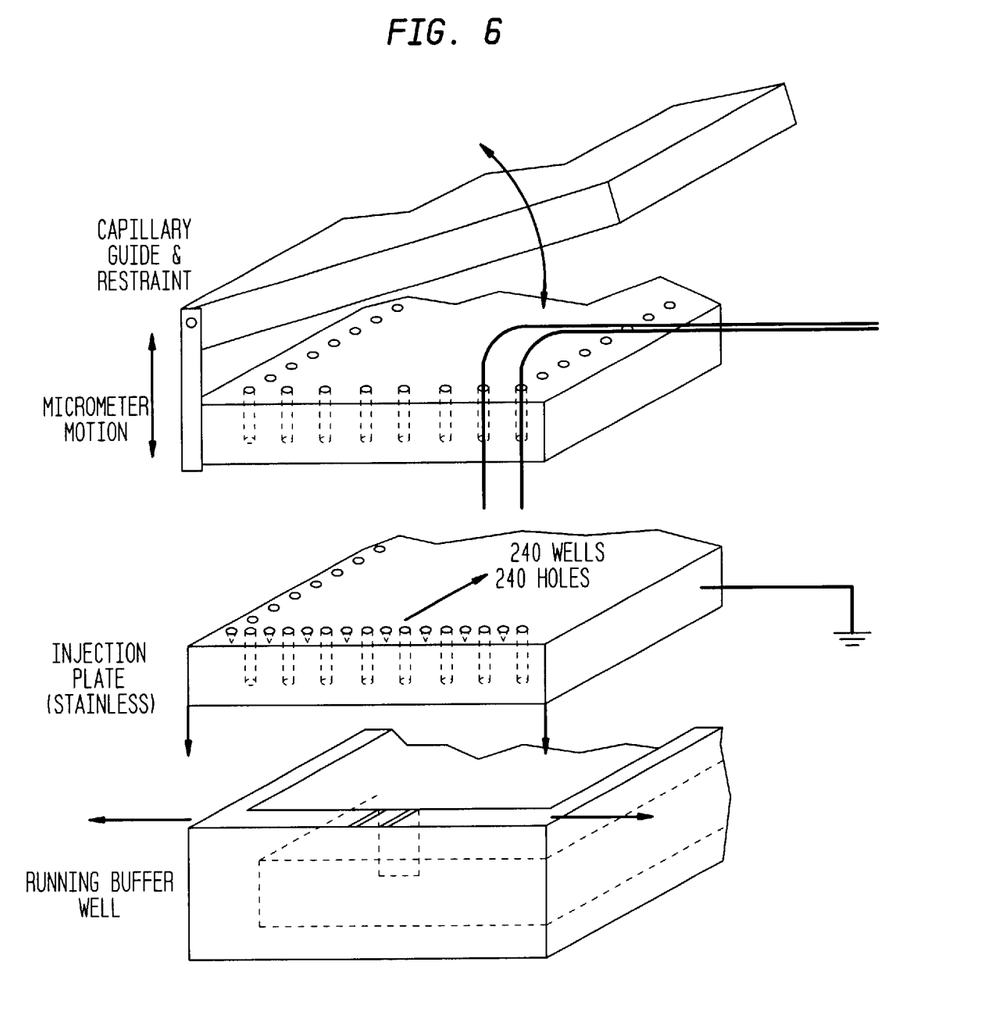
FIG. 6 is a schematic diagram of an electrokinetic injection assembly illustrating the capillary guide plate, the stainless steel injection plate, and the running buffer reservoir.

The capillaries can be loaded using electrokinetic injection. Each quadrant has its own loading area which allows injection of a total of 1024 samples. The injector (FIG. 6) contains three sections, a top lucite plate with 256 holes, a stainless steel plate with 256 wells and a bottom buffer reservoir. The cathode ends of the capillaries were threaded into guide holes in the lucite plate. A restraining plate was lowered on the capillaries, causing them to bend above the point of entry. Samples are placed in the wells of the stainless steel plate and the injection plate is positioned so the capillary tips were centered on the injection wells. The array is self-leveled by lowering the capillary guide plate until all of the capillaries made contact with the bottom of their respective sample wells. The whole group of capillaries is raised by approximately 600 µm, placing the tips near the middle of the sample volume, and the samples are injected at 100 V/cm. After loading, the capillaries are raised, the well plate is removed, and the capillaries are lowered into the running buffer, which is positioned immediately below the well plate. The sequencing samples may then be electrophoresed at 140 V/cm.

Data Analysis

Data obtained using the rotary scanner and four-color confocal detection system is summed post-run into individual capillary files. The sequence data are analyzed and base-called using BaseFinder, as described in M. C. Giddings et al., *Genome Research*, Vol. 6, pg. 644–665 (1998). BaseFinder uses a set of modules, each with user-input parameters, to define a script which can be saved and used on multiple runs. These scripts consist of primer peak deletion, baseline correction, spectral separation using a multicomponent matrix transformation, noise filtering and deconvolution, histogram equalization, mobility shift correction, and base calling. The primer peak is identified automatically by the program and the data preceding the primer deleted. The baseline correction is performed with a moving window of 350 points. The color-separated data are Gaussian-filtered and normalized. Identical filtering and base-calling parameters are used for 80% of the capillary runs; the parameters have to be reoptimized for the other data files. A typical set of parameters used are described in the following section. Identical nonlinear mobility shifts are applied to each file prior to base-calling.

EXAMPLES

Figure 8:
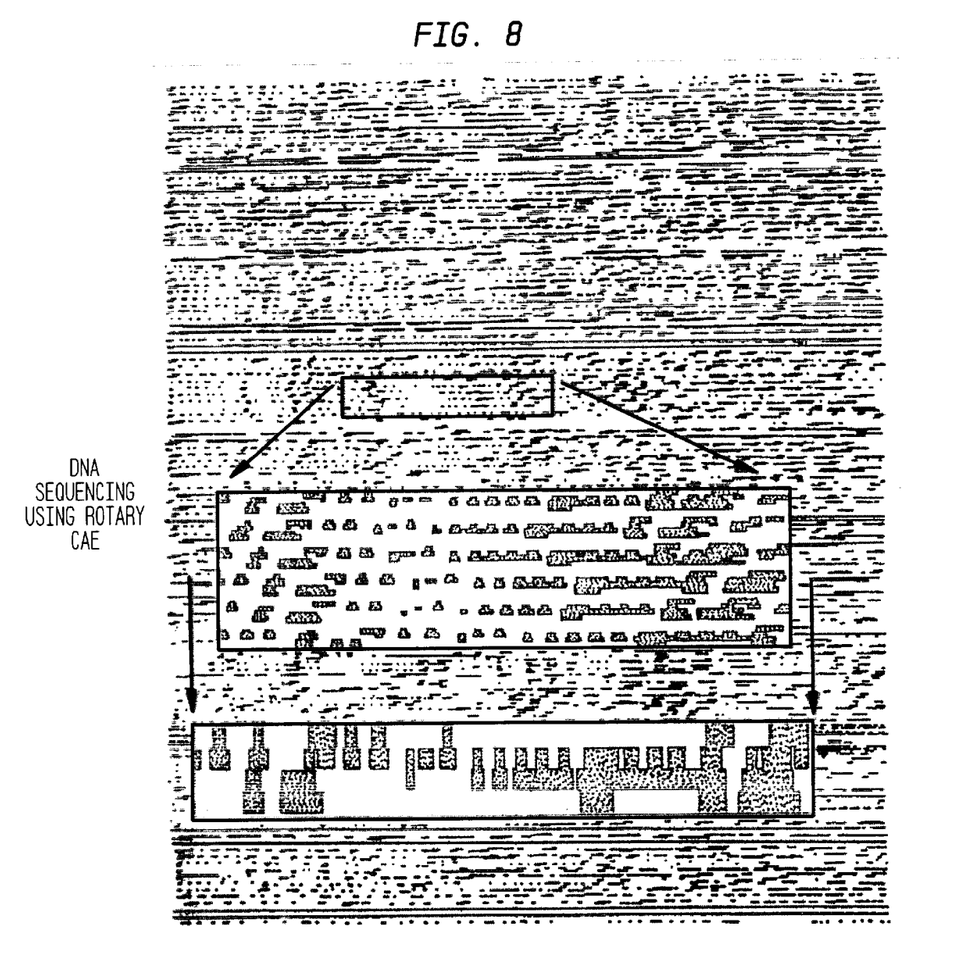
FIG. 8 is an image of sequencing data obtained from 128 capillaries using the rotary scanner of the invention, wherein each capillary is represented using four lanes, one for each base.

FIG. 8 presents unprocessed image data of M13mp18 sequencing separations performed on 128 capillaries run on the rotary capillary array scanner. Each capillary is represented using four lanes, one for each base. The total electrophoresis time is 130 min. To prepare this image from the text data files, the four-column 12-bit electrophoresis data were opened in NIH Image as 8-bit text files and saved as 4-pixel-wide 8-bit TIFF files. These files were enlarged to 16 pixels for ease of visualization and then color-contrasted in Photoshop.

For ease of sample loading, four bundles of 32 capillaries were placed in the first quadrant of the scanner. Each capillary in this image is represented by four different color lanes, one for each base. The sequence data in each capillary is aligned at base position 280 and 14 min of data for each capillary are presented. The sequencing bands are observed in more than one lane for some of the bases due to the spectral overlap of the primers. This spectral overlap is corrected by the multidimensional matrix script in BaseFinder. The insets in FIG. 8 show an expanded view of the capillaries from the third bundle. The bands in the pentet and quartet region at base positions 323–332 are resolved and the highest intensity band represents the terminating nucleotide. Ten of the 128 capillaries shown in FIG. 7 were broken or clogged during the process of array fabrication and loading, and could not be filled with the sieving matrix; broken capillaries were closed off with epoxy. These capillaries are marked with an asterisk (*) in the image in FIG. 7. The sequence data from the remaining 118 capillaries were analyzed and base-called. We did not perform repeated runs with improved samples and new capillaries to optimize the overall electrophoretic performance. The results of our first complete 128-capillary run are presented and discussed here for the purpose of illustrating scanner capabilities.

Figure 9:
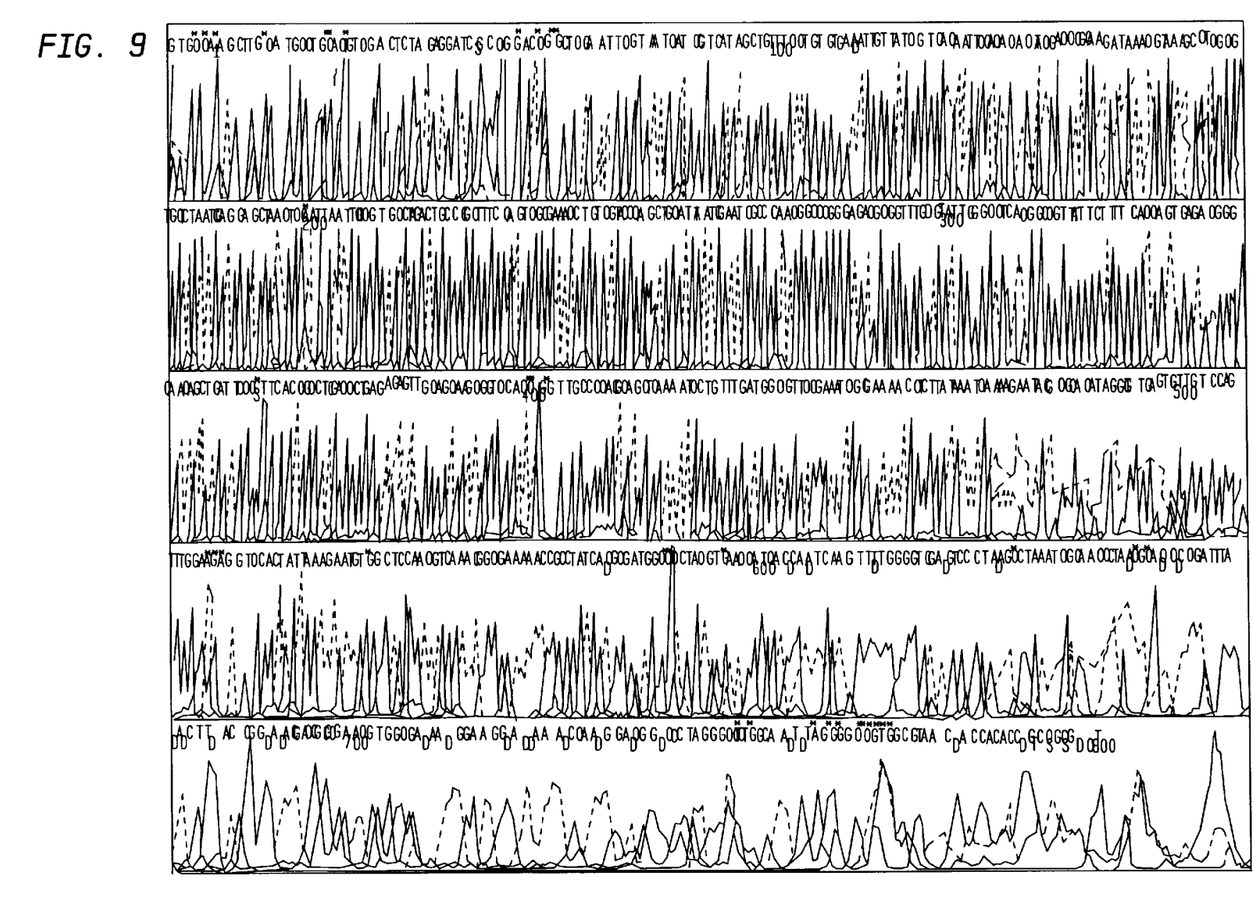
FIG. 9 depicts the complete DNA sequence data from capillary 64 in FIG. 8. Compressions in this figure are marked with an *, substitution errors by S, insertion errors by I and deletion errors as D.

The 12-bit text sequence data obtained from the scanner were averaged over two cycles and base-called using BaseFinder. The background-subtracted, color-separated, mobility-shift-corrected, and base-called data from capillary 64 is presented in FIG. 8. The data can be read and called starting at position 18 past the primer and extend to over 800 bases. Electrophoretic runs from injection to 800 bases typically required 140 min of data acquisition. The base-calling program read 675 bases with 94% accuracy and 750 bases with 90% accuracy. The script steps used to analyze these data included primer peak deletion, baseline subtraction, spectral separation, two rounds of successive noise filtering (first round: window width M=10, Gaussian width σ=2.8; second round: M=10, σ=1.8) and deconvolution with the default spread function, a final noise filtering (M=10, σ=1.5), normalization of the signal intensities, histogram equalization to cut off spurious peaks, mobility shift correction and finally base calling. The final base-calling module used evenly weighted base spacing, peak width, and peak height parameters. Beginning, end, and spacing tolerances were set to 1.7, 1.6, and 2.4, respectively. The electrophoresis runs presented here were performed at room temperature and therefore several compressions were observed and are marked with an * in FIG. 9. Substitution, deletion and insertion errors are also marked with an S, D, and 1, respectively, in FIG. 9.

Figure 10:
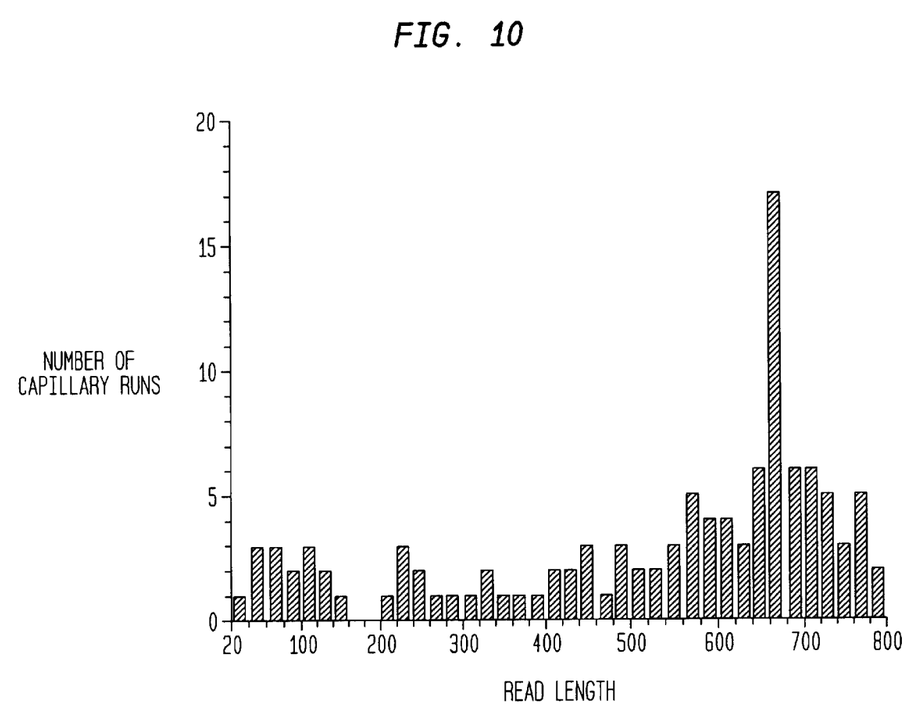
FIG. 10 is a histogram showing numbers of capillaries versus the read length at 90% accuracy. This figure displays results from 113 good capillaries of a 128 capillary array, and includes the compressions shown in FIG. 9.

The sequence data from the 118 good capillaries were analyzed for sample injection and base-calling efficiency. The injection was unsuccessful for capillaries 2, 3, 19, 49 and 88. The injection efficiency was thus 96%. FIG. 10 presents the histogram of the number of capillaries vs. the read lengths where the read length is determined by the 90% accuracy threshold. Read lengths greater than 500 bases were obtained in 60% of the capillaries. These read lengths are similar to those obtained using commercial 96 CAE instruments. The reduced base-calling accuracy in these runs is primarily a result of the compressions at positions 21–24, 30, 38–41, 64–70, 198–199, 356–357, 400–403, 513–516, 539, 585–586, 594, 641, and 660–62. These positions are marked with an * in FIG. 9. The remaining substitution, insertion, and deletion errors were mostly made in the low resolution regions past 600 bases. The compressions can be eliminated by running the sequencing separations at higher temperatures or by using alternate chemistries such as replacing guanine with inosine in the sequencing reactions. The use of elevated temperatures for DNA sequencing also results in improved resolution for longer fragments. If the errors due to compressions listed above are excluded for the run presented in FIG. 9, the accuracy rate is 99.5% at 600 bases and 98% at 675 bases. The 90% accuracy threshold data presented in FIG. 10 includes the errors due to compressions. If the compressions are excluded from the accuracy calculations to simulate results expected from elevated temperature runs, then the projected accuracy rate for the histogram in FIG. 10 will be approximately 94%.

What is claimed is:

1. A rotary capillary array scanner, the scanner comprising:
   a source of radiant energy of a first wavelength;
   one or more cylinders having a common vertical axis;
   a plurality of capillaries disposed along the circumferences of the one or more cylinders such that a length of the capillaries is substantially parallel to the vertical axis;
   an objective lens housed within the one or more cylinders, capable of focusing radiant energy of the first wavelength onto the capillaries and capable of receiving radiant energy of a second wavelength emitted from the capillaries;
   a rotor which rotates the objective lens along the circumference of the one or more cylinders;
   a beam splitter capable of passing radiant energy of the second wavelength and rejecting radiant energy of the first wavelength;
   a detector capable of measuring the intensity of the radiant energy passed from the beam splitter.

2. The scanner of claim 1, wherein the objective lens is housed within two cylinders.

3. The scanner of claim 1, further comprising a computer for controlling the rotor and processing intensity measurements made by the detector.

4. The scanner of claim 1, wherein the rotor is connected to a micro-stepping indexed motor.

5. The scanner of claim 1, further comprising a quarter-wave plate positioned in the path of the radiant energy of the first wavelength before the objective lens focuses the energy onto the capillaries.

6. The scanner of claim 1, further comprising a photodiode, wherein the radiant energy of a first wavelength causes the detector to initiate intensity measurements by illuminating the diode.

7. The scanner of claim 1, further comprising four posts, to which the one or more cylinders are rigidly attached.

8. The scanner of claim 7, wherein the four posts are approximately equally spaced by four rings, each of which divides the one or more cylinders into approximately equal quadrants.

9. The scanner of claim 8, wherein each quadrant of the one or more cylinders has from about 200 to 300 grooves to accommodate the capillaries.

10. The scanner of claim 9 wherein each groove is spaced approximately 250 to 300 $\mu$m apart and is 100 to 150 $\mu$m deep.

11. The scanner of claim 8, wherein each ring supports at least one fixture for holding the capillaries in place against the grooves.

12. The scanner of claim 7, further comprising a disk mounted on the rotor, wherein the disk has a photodiode positioned at its edge and a slot disposed at least partway along an axis defining a radius of the disk, such that rotation of the slot provides a pulse to enable data acquisition.

13. The scanner of claim 1, wherein the source of radiant energy is a coherent light source.

14. The scanner of claim 13, wherein the coherent light source is a laser.

15. A rotary capillary array scanner, the scanner comprising:
   a source of radiant energy of a given wavelength;
   one or more cylinders having a common vertical axis;
   a plurality of capillaries disposed along the circumferences of the one or more cylinders such that a length of the capillaries is substantially parallel to the vertical axis;
   an objective lens housed within the one or more cylinders, capable of focusing radiant energy of the given wavelength onto the capillaries and capable of receiving radiant energy of different wavelengths reflected from the capillaries;
   a rotor which rotates the objective lens along the circumference of the one or more cylinders;
   a plurality of beam splitters, each capable of passing the radiant energy emitted from the capillaries at wavelengths different from other beam splitters in the scanner and capable of rejecting all other wavelengths;
   a plurality of photodetectors, each capable of measuring the intensity of radiant energy passed to it by one of the beam splitters.

16. The scanner of claim 15, wherein the objective lens is housed within two cylinders.

17. The scanner of claim 15, further comprising a computer for controlling the rotor and processing intensity measurements made by the detector.

18. The scanner of claim 15, wherein the rotor is connected to a micro-stepping indexed motor.

19. The scanner of claim 15, further comprising a quarter-wave plate positioned in the path of the radiant energy of the first wavelength before the objective lens focuses the energy onto the capillaries.

20. The scanner of claim 15, further comprising a photodiode, wherein the radiant energy of a first wavelength causes the detector to initiate intensity measurements by illuminating the diode.

21. The scanner of claim 15, further comprising four posts, to which the one or more cylinders are rigidly attached.

22. The scanner of claim 15, wherein the four posts are approximately equally spaced by four rings, each of which divides the one or more cylinders into approximately equal quadrants.

23. The scanner of claim 22, further comprising a disk mounted on the rotor, wherein the disk has a photodiode positioned at its edge and a slot disposed at least partway along an axis defining a radius of the disk, such that rotation of the slot provides a pulse to enable data acquisition.

24. The scanner of claim 22, wherein each quadrant of the one or more cylinders has from about 200 to 300 grooves to accommodate the capillaries.

25. The scanner of claim 22, wherein each groove is spaced approximately 250 to 300 $\mu$m apart and is 100 to 150 $\mu$m deep.

26. The scanner of claim 22, wherein each ring supports at least one fixture for holding the capillaries in place against the grooves.

27. The scanner of claim 26, wherein the coherent light source is a laser.

28. The scanner of claim 15, wherein the source of radiant energy is a coherent light source.

29. The scanner of claim 15, further comprising four photodetectors.

30. A method for detecting fluorescence from organic analytes electrophoretically separated in a plurality of capillaries, the method comprising the steps of positioning the capillaries around the circumference of at least one cylinder;

providing a source of radiant energy of a first wavelength, focusing, through an objective lens, the radiant energy of the first wavelength onto a capillary so that the radiant energy illuminates analytes within the capillary;

receiving, through the objective lens, radiant energy of a second wavelength from the analytes;

passing radiant energy of the second wavelength from the objective lens through a dichromic beamsplitter, rejecting radiant energy of all other wavelengths thereby;

passing radiant energy of the second wavelength from the dichroic beamsplitter to a photodetector;

measuring the intensity of radiant energy of the second wavelength with the photodetector;

rotating the objective lens around the circumference of the at least one cylinder to place another capillary within the path of radiant energy of the first wavelength;

repeating the steps of focusing, receiving, and measuring the radiant energy and rotating the objective lens until all desired capillaries have been placed within the path of the radiant energy.

* * * * *